United States Patent [19]

Young

[11] 4,325,370
[45] Apr. 20, 1982

[54] DISPOSABLE DEVICE FOR FIXATION OF THE BARIUM ENEMA TIP

[75] Inventor: Ruperto S. Young, Amsterdam, N.Y.

[73] Assignees: Janis Marie Young, Amsterdam; Roberta H. Wessendorf, Guilderland, both of N.Y.

[21] Appl. No.: 254,141

[22] Filed: Apr. 14, 1981

[51] Int. Cl.³ .......................................... A61M 25/02
[52] U.S. Cl. .................................. 128/245; 128/227; 128/658; 128/DIG. 26
[58] Field of Search ............. 128/239, 227, 245, 246, 128/98, 348–350, 654–658, 291, 283

[56] References Cited

U.S. PATENT DOCUMENTS

| | | | |
|---|---|---|---|
| 2,080,788 | 5/1937 | Ross | 128/227 |
| 2,528,095 | 10/1950 | Ward | 128/227 |
| 2,586,940 | 2/1952 | Graham | 128/DIG. 26 |
| 3,581,732 | 6/1971 | Ruiz | 128/658 |
| 3,765,401 | 10/1973 | Vass | 128/1 R |
| 3,990,448 | 11/1976 | Mather et al. | 128/339 |
| 4,020,835 | 5/1977 | Nordstrom et al. | 128/214.4 |
| 4,057,066 | 11/1977 | Taylor | 128/349 R |
| 4,248,229 | 2/1981 | Miller | 128/245 |

Primary Examiner—Dalton L. Truluck
Attorney, Agent, or Firm—Walter F. Wessendorf, Jr.

[57] ABSTRACT

Discloses a device for the external fixation of the barium enema tip inserted into the patient's rectum. The device has a waist band, anterior and posterior straps suitably attached to the waist band a locking ring for releasable and removable locking engagement with a locking groove on the barium enema tip. The barium enema tip has a lumen communicating with side holes, a proximal end having a raised ridge to thereby receive and retain enema-bag tubing, a distal end, and an hourglass shaped cuff having a concave portion whereby the anal sphincter complementally receives and locks thereon to prevent leakage of barium liquid.

7 Claims, 4 Drawing Figures

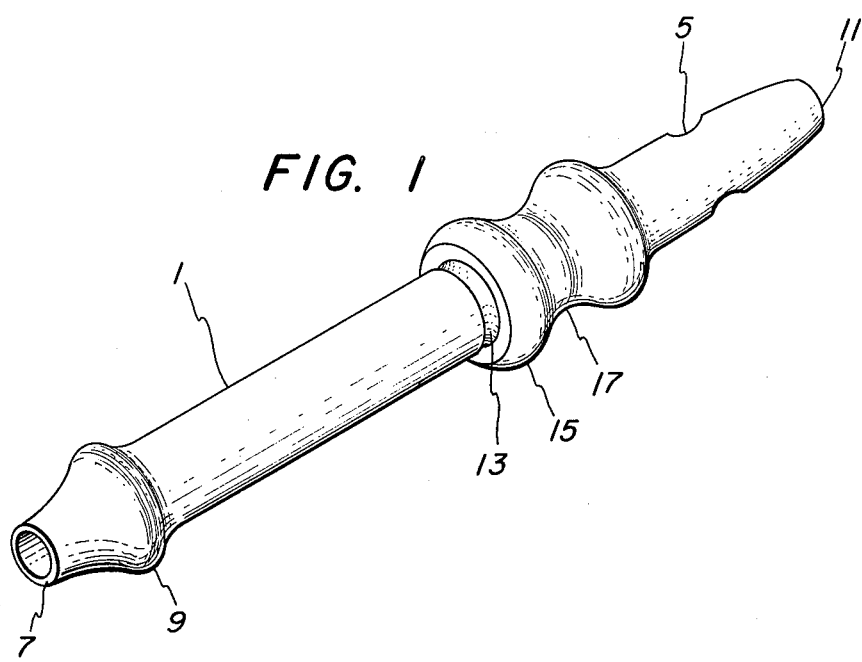
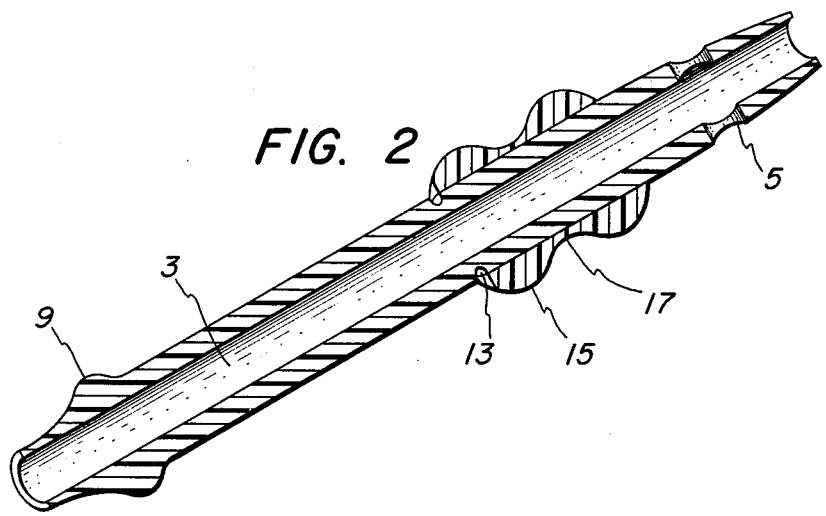

DISPOSABLE DEVICE FOR FIXATION OF THE BARIUM ENEMA TIP

BACKGROUND OF THE INVENTION

1. Technical Field

This invention relates to a disposable device fo fixation of the barium enema tip.

Barium enema is an x-ray procedure where a contrast material, barium sulfate, is introduced through the rectum and the examination is performed after the colon is filled with an adequate amount of the liquid barium. The introduction of this liquid is accomplished with a certain amount of pressure to overcome the natural colonic resistance to distension and to overcome the natural flow of intestinal contents. Consequently, the prior-art tube or tip used for this study can be easily dislodged by the pressure and more so with the positioning and manipulation of the patient, which is necessary for such study. On occasion, the tip may be inserted too far into the rectum and cause bowel injury. In the present state of the art, an intrarectal balloon is used for retention of the enema tip. This prior-art device has been known to cause injury and perforation of the rectum and is also known to obscure anal or rectal pathology, in that, it creates an intrarectal abnormal shadow on radiologic film.

Accordingly, the object of the invention is to contribute to the solution of the problems of the prior art by providing a device for external fixation of the barium enema tip where there is no inconvenience to the patient or for personnel, with a vastly simpler procedure; where overextension of the barium enema tip into the rectum resulting in perforation of the rectum is checked; where dislodgement of the enema tip during examination is prevented; where the use of the balloon-type enema tip which can obscure pathology is avoided; where barium leakage around the tip is prevented.

SUMMARY OF THE INVENTION

In accordance with the invention, there is provided an external fixation device in the form of an elastic waist band, an anterior elastic strap fitting snugly against the body and running from the inner, upper thighs to the waist whereat the anterior elastic strap is attached, a stretchable mesh cloth attached to the region bounded by the waist band and anterior elastic strap to cover the genital area, posterior elastic straps fitting snugly against the body and running around the buttocks area to the waist where the posterior straps are attached, and a spring locking ring attached to the anterior and posterior straps for removable locking engagement with a locking groove in the barium enema tip inserted in the rectum. The barium enema tip has an hour-glass shaped cuff which is complementally received by the anal sphincter which locks itself upon the concave portion of such cuff to prevent barium leakage around the enema tip.

BRIEF DESCRIPTION OF THE DRAWINGS

This object and other objects of the invention should be discerned and appreciated by reference to the drawings wherein like reference numerals refer to similar parts throughout the several views, in which:

FIG. 1 is an isometric view of the barium enema tip;

FIG. 2 is an isometric view of the barium enema tip in cross section;

DESCRIPTION OF THE PREFERRED EMBODIMENT

Figure 3:
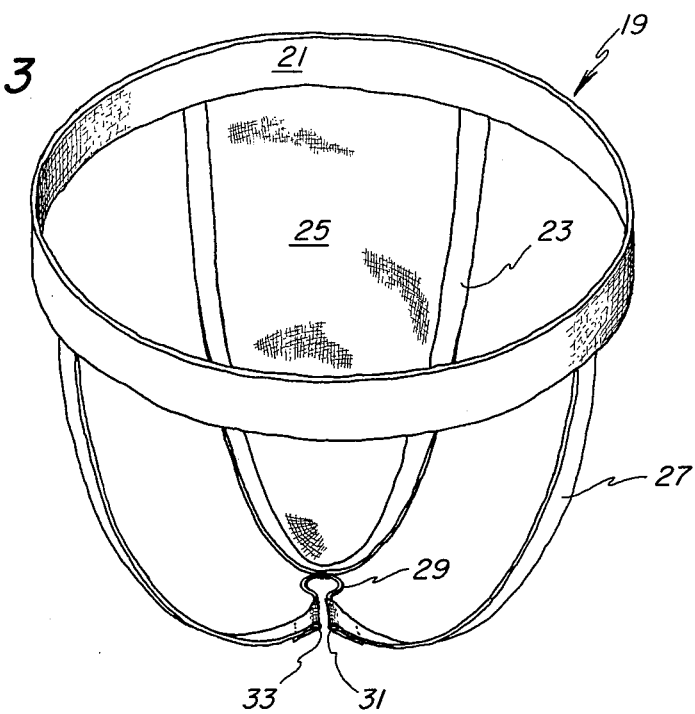
FIG. 3 is a view of the external fixation device.
Figure 4:
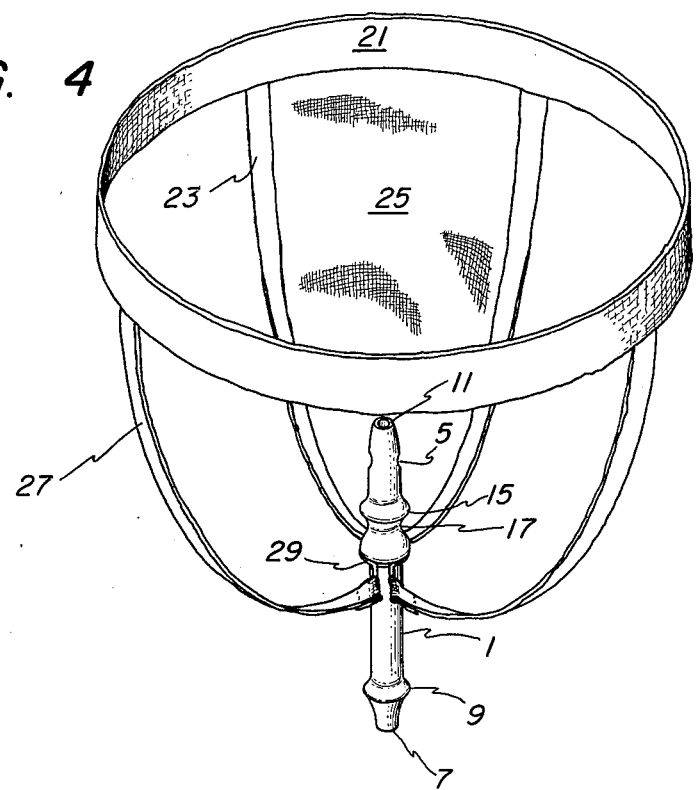
FIG. 4 is a view of the external fixation device assembled in locking engagement with the barium enema tip.

FIG. 1 of the drawings shows the barium enema tip 1 of suitable plastic that is pliable. Barium enema tip 1 has a lumen 3, side holes 5 communicating with lumen 3, a proximal end 7 with a raised ridge 9, a distal end 11, locking groove 13 and an hour-glass shaped cuff 15, of soft compressible material, having a concave portion 17. Tubing from the enema bag receives the proximal end 7 therein with retention provided and effected by the raised ridge 9. Upon sufficient insertion of the barium enema tip 1 into the rectum of the patient by means of initially inserting the distal end 11, the anal sphincter complementally receives and locks upon the concave portion 17 of cuff 15 to thereby prevent barium leakage around the enema tip.

The external fixation device 19 has an elastic waist band 21, an anterior elastic strap 23 fitting snugly against the body and running from the inner, upper thighs to the waist where the anterior elastic strap 23 is suitably attached, a stretchable mesh cloth 25 suitably attached to the region bounded by the waist band 21 and anterior elastic strap 23 to cover the genital area of the patient, posterior elastic straps 27 fitting snugly against the body and running around the buttocks area to the waist where the posterior straps 27 are suitably attached, and a spring locking ring 29 suitably attached to the anterior and posterior straps 23 and 27, as shown, for removable locking engagement with the locking groove 13 in the barium enema tip 1. Spring locking ring 29 is in the form of a split ring defining prongs 31 and 33 to which the posterior straps 27 are attached.

The patient appropriately puts on the external fixation device 19 so that same will occupy the spatial relationship to the body as described herein. The device 19 also serves as an undergarment for the patient, preserving some degree of privacy for the patient with the mesh cloth 25 covering the patient's genital area. With the barium enema tip 1 inserted sufficiently into the patient's rectum in order that his anal sphincter complementally receives said locks upon the concave portion 17 of cuff 15, the spring locking ring 29 is appropriately positioned on groove 13 for locking engagement therewith. To release the spring locking ring 29 from groove 13, the lowermost portions of the posterior elastic straps 27 are appropriately manipulated to move-apart the prongs 31 and 33 to thereby release the ring 29 from groove 13.

From the foregoing description it should be appreciated that the patient himself can easily put on the external fixation device 19, appropriately insert the barium enema tip 1 safely into his rectum to the extent that his anal sphincter receives and locks upon the concave portion 17 of cuff 15 and simply dispose ring 29 into locking engagement with groove 13 to prevent dislodgement of the enema tip during examination.

The device is particularly desirable for the pediatrics patient when the balloon is not reccommended. And its use in the reduction of intussuception of the young infant will be valuable.

Having thusly described my invention, I claim:

1. The combination of a barium enema tip and a device for the external fixation of said barium enema tip, said barium enema tip being insertable into a patient's rectum to perform the x-ray procedure whereby a contrast material is introduced through the rectum and the examination is performed after the colon is filled with an adequate amount of barium liquid, said device being of integral, one-piece construction and comprising a waist band, anterior strap, posterior straps and locking ring, said anterior strap being in attached relationship with said waist band, said posterior straps being in attached relationship with said waist band, said anterior and posterior straps being in attached relationship with said locking ring, said barium enema tip having, in circumferential relationship, a locking groove on its external surface, said locking ring being a split ring engageable with said locking groove to effect removable locking engagement therewith during use, said waist band of said device when put on and worn by said patient fitting snugly against the waist, said anterior strap fitting snugly against the body and running from the inner, upper thighs to said waist, and said posterior straps fitting snugly against the body and running around the buttocks area to said waist, said barium enema tip having an hour-glass shaped cuff having a concave portion thereby and whereby, upon said barium enema tip being inserted into the patient's rectum, the patient's anal sphincter will complementally receive and lock upon said concave portion of said cuff to prevent leakage of barium liquid around said barium enema tip.

2. The combination of claim 1 wherein said waist band, anterior and posterior straps are of elastic material.

3. The combination of claim 1 wherein said device has a mesh cloth for covering the patient's genital area.

4. The combination of claim 1 wherein said waist band and anterior strap define a genital-area region and carry therefor in attached relationship a mesh cloth for covering the patient's genital area.

5. The combination of claim 1 wherein said barium enema tip has a lumen communicating with side holes, a proximal end having a raised ridge to thereby receive and retain tubing from an enema bag, and a distal end.

6. The combination of claim 1 wherein said split ring defines prongs and wherein said posterior straps are in attached relationship with said prongs.

7. The combination of claim 1 wherein said waist band, anterior and posterior straps are of elastic material, wherein said waist band and anterior strap define a genital-area region and carry therefor in attached relationship a mesh cloth for covering the patient's genital area, wherein said barium enema tip has a lumen communicating with side holes, a proximal end having a raised ridge to thereby receive and retain tubing from an enema bag, and a distal end, and wherein said split ring defines prongs and wherein said prongs are in attached relationship with said prongs.

* * * * *